(12) United States Patent
Klewinghaus et al.

(10) Patent No.: US 11,571,502 B2
(45) Date of Patent: Feb. 7, 2023

(54) PRESSURE MEASURING LINE AND METHOD FOR MONITORING THE SAME WITH SUITABLE DEVICES AND APPARATUSES

(71) Applicant: Fresenius Medical Care Deutschland GmbH, Bad Homburg (DE)

(72) Inventors: Juergen Klewinghaus, Oberursel (DE); Alexander Schroers, Frankfurt am Main (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 30 days.

(21) Appl. No.: 17/049,117

(22) PCT Filed: Apr. 16, 2019

(86) PCT No.: PCT/EP2019/059835
§ 371 (c)(1),
(2) Date: Oct. 20, 2020

(87) PCT Pub. No.: WO2019/201943
PCT Pub. Date: Oct. 24, 2019

(65) Prior Publication Data
US 2021/0236709 A1    Aug. 5, 2021

(30) Foreign Application Priority Data
Apr. 20, 2018   (DE) .................. 102018109563.5

(51) Int. Cl.
*A61M 1/36*    (2006.01)
*A61M 1/14*    (2006.01)

(52) U.S. Cl.
CPC ........ *A61M 1/3639* (2013.01); *A61M 1/3627* (2013.01); *A61M 2205/18* (2013.01); *A61M 2205/3331* (2013.01)

(58) Field of Classification Search
CPC .............. A61M 1/3639; A61M 1/3627; A61M 2205/18; A61M 1/3641;
(Continued)

(56) References Cited

U.S. PATENT DOCUMENTS 4,240,294 A * 12/1980 Grande ..................... G01F 1/38
                                                        73/861.47
6,623,443 B1    9/2003 Polaschegg
(Continued)

FOREIGN PATENT DOCUMENTS

DE        3442744        6/1986
DE        19901078       2/2000
(Continued)

OTHER PUBLICATIONS

Beden, A Method of Checking a Connection State of a Blood Treatment Device With a Blood Tubing Set, and Devices, 2016, PGPUB Translation (Year: 2016).*
(Continued)

*Primary Examiner* — Quang D Thanh
*Assistant Examiner* — Brandon W. Levy
(74) *Attorney, Agent, or Firm* — Fish & Richardson P.C.

(57) ABSTRACT

A pressure measuring line with a connector can be used to connect the pressure measuring line to a blood treatment apparatus, and to a membrane. In some embodiments, the pressure measuring line comprises at least two consecutive lumen sections, namely the first lumen section and the second lumen section. The first lumen section can include a first lumen geometry and the second lumen section can include a second lumen geometry. The first lumen geometry and the second lumen geometry can differ from each other in at least their diameters. Further, a monitoring method and devices can be used in conjunction with the pressure measuring lines.

27 Claims, 6 Drawing Sheets

(58) Field of Classification Search
CPC ...... A61M 2205/3331–3362; G01F 1/34–386; G01F 1/00; G01F 3/00; G01F 5/00; G01F 1/44

See application file for complete search history.

(56) References Cited

U.S. PATENT DOCUMENTS

| | | |
|---|---|---|
| 2009/0152179 A1 | 6/2009 | Kopperschmidt |
| 2012/0083726 A1 | 4/2012 | Kopperschmidt et al. |
| 2013/0028788 A1 | 1/2013 | Gronau et al. |
| 2013/0150813 A1 | 6/2013 | Gordon et al. |
| 2018/0024022 A1 | 1/2018 | Beden |
| 2019/0275229 A1 | 9/2019 | Muller et al. |

FOREIGN PATENT DOCUMENTS

| | | | | |
|---|---|---|---|---|
| DE | 102009024465 | 1/2011 | | |
| DE | 102011108784 | 4/2013 | | |
| DE | 102015102040 | 8/2016 | | |
| DE | 102016109340 | 11/2017 | | |
| JP | H02-289259 | 11/1990 | | |
| JP | 2002-095741 | 4/2002 | | |
| JP | 2005195557 A | * 7/2005 | .......... | A61M 1/3641 |
| JP | 2007-282928 | 11/2007 | | |
| WO | WO 2013/017236 | 2/2013 | | |
| WO | WO 2014/099779 | 6/2014 | | |

OTHER PUBLICATIONS

Nakagawa, Protection Filter of Pressure Converter Detecting Liquid Seepage, 2005, PGPUB Translation (Year: 2005).*
Masataka, Method for Detecting Mal-Mounting of Membrane Filter, 1990, Espacenet Translation (Year: 1990).*
PCT International Preliminary Report on Patentability in International Appln. No. PCT/EP2019/059835, dated Oct. 29, 2020, 15 pages (with English translation).
PCT International Search Report and Written Opinion in International Appln. No. PCT/EP2019/059835, dated Jul. 23, 2019, 20 pages (with English translation).

* cited by examiner

PRESSURE MEASURING LINE AND METHOD FOR MONITORING THE SAME WITH SUITABLE DEVICES AND APPARATUSES

CROSS-REFERENCE TO RELATED APPLICATIONS

The present application is the national stage entry of International Patent Application NO. PCT/EP2019/059835, filed on Apr. 16, 2019, and claims priority to Application No. DE 10 2018 109 563.5, filed in the Federal Republic of Germany on Apr. 20, 2018, the disclosures of which are expressly incorporated herein in their entirety by reference thereto.

FIELD OF THE INVENTION

In some embodiments, the present disclosure relates to a pressure measuring line. It also relates to a blood chamber and an extracorporeal blood tubing set. It further relates to a detection device, a blood treatment apparatus as well as a method for monitoring a pressure measuring line. Furthermore, the present disclosure relates to a digital storage medium, a computer program product as well as a computer program.

BACKGROUND

Connecting an extracorporeal blood circuit to a pressure sensor in order to measure the pressure in the blood circuit, via a pressure measuring line that forks from the blood circuit, is already known in the prior art. The pressure sensor is regularly part of a blood treatment apparatus. The pressure measuring line, which is usually a spur line, is connected to the pressure sensor. A certain amount of air is always contained in it by which the pressure is measured via the pressure sensor. To prevent the unwanted advancement of blood into the blood treatment machine at least one hydrophobic protective filter is positioned in the line, this is in the form of a membrane or comprises such. This hydrophobic filter, together with the remaining blood tubing set of the extracorporeal blood circuit, is discarded after a completed blood treatment.

While an extracorporeal blood circuit is in operation it may occur that the hydrophobic filter gets wet with blood and, therefore, it becomes at least partly clogged. This results in an impairment of the functionality of the pressure measurement. Whenever the user is confronted with this problem, he must exchange the hydrophobic filter for a new hydrophobic filter. The new hydrophobic filter may be a spare part or be contained in a spare part. It may, particularly, be a spare pressure measuring line, which is configured to be attached to a free end of the blood chamber or the bubble trap. Then the entire extracorporeal blood tubing set does not need to be changed.

SUMMARY

In some embodiments, the present disclosure describes a further pressure measuring line and a method for monitoring a pressure measuring line. In addition, suitable devices and apparatuses, a suitable digital storage medium, a suitable computer program product and a suitable computer program for carrying out the method are described herein.

Advantages of the present disclosure are achieved by a pressure measuring line as described herein. Advantages are further achieved by a blood chamber having the features described herein and by an extracorporeal blood tubing set having the features described herein. Advantages are also achieved by a detection device, a blood treatment apparatus, and a method for monitoring a pressure measuring line as described herein. Furthermore, advantages are achieved by a digital storage medium, by a computer program product, and by a computer program having the features described herein.

According to the present disclosure, a pressure measuring line is described herein as having an optional membrane and having a connector to connect the pressure measuring line to a blood treatment apparatus for blood treatment, whereby the latter optionally comprises a compressed air outlet. The connector is optionally designed to connect the pressure measuring line to an outlet of the blood treatment apparatus, preferably to the compressed air outlet.

According to the present disclosure, the pressure measuring line comprises at least two consecutive lumen sections, namely a first lumen section and a second lumen section. The first lumen section here comprises a first lumen geometry. The second lumen section comprises a second lumen geometry. The first and the second lumen geometries differ from each other in at least their diameters or only in their diameters.

The blood chamber according to the present disclosure comprises a pressure measuring line according to the present disclosure or is connected to it. The blood chamber may, for example, be configured to be or to become installed in a blood withdrawal line and/or in a blood return line of an extracorporeal blood circuit.

The blood chamber according to the present disclosure may be an arterial and/or venous blood chamber.

The extracorporeal blood tubing set according to the present disclosure comprises at least a blood chamber according to the present disclosure and/or a pressure measuring line according to the present disclosure or is connected to at least one of these two devices.

According to the present disclosure, a detection device is proposed that is programmed and/or configured to carry out or initiate a method for monitoring a pressure measuring line of an extracorporeal blood tubing set.

The method can be performed while a blood treatment apparatus is connected to a pressure measuring line of an extracorporeal blood tubing set via a connection point. Furthermore, the treatment apparatus is embodied with a pressure sensor that is positioned to measure the pressure in the pressure measuring line.

In further method steps the pressure sensor carries out a measurement of the pressure in the pressure measuring line, or of a pressure change over time, as well as a determining of a deviation variable or deviation parameter (alternatively: "deviation degree") of the pressure or of its change.

Furthermore, the deviation variable of the measured pressure, or the change thereof over time, is in each case evaluated by a comparison of the determined deviation variable or its changes with previously measured or stored values, threshold values, ranges or courses therefor.

Thereby, the deviation variable as a square of the standard deviation may be understood as a measure of the variability of the pressure.

In general, the deviation variable (or "deviation degree") may be understood as a measure of the variability of the pressure, and/or as a measure of how much a measured pressure value deviates from an expected value or anticipated value, such as an average value, obtained from past measurements. The degree of the deviation may lead as a mathematical value to a statement ("too large", "within specified limits", etc.) or can be used therefor.

The blood treatment apparatus according to the present disclosure comprises at least one extracorporeal blood tubing set according to the present disclosure and/or one detection device according to the present disclosure, or is at least connected to at least one of these two devices.

The methods according to the present disclosure serve for monitoring a pressure measuring line of an extracorporeal blood tubing set.

The methods comprise provision of a blood treatment apparatus with a connection point that is embodied to be connectable to a pressure measuring line of an extracorporeal blood tubing set. Furthermore, the blood treatment apparatus is embodied with a pressure sensor that is positioned to measure the pressure in the pressure measuring line.

In further method steps, the pressure sensor carries out a measurement of the pressure in the pressure measuring line, or of a pressure change over time, and determines a deviation variable of the pressure or of its change.

Furthermore, the deviation variable of the measured pressure, or the change thereof over time, is in each case evaluated by a comparison of the determined deviation variable or its change with the previously measured or stored values, threshold values, ranges or courses.

A digital, particularly non-volatile storage medium, according to the present disclosure, particularly in the form of a machine-readable medium, particularly in the form of a floppy disk, CD, DVD or in the form of a USB-stick or EPROM, particularly with electronically or optically readable control systems, can interact with a programmable computer system, in such a way that the machine-induced steps of a method according to the present disclosure are initiated.

A computer program product according to the present disclosure comprises a volatile, transient program code or one stored on a machine-readable medium or a signal wave to initiate the machine-induced steps of the method according to the present disclosure, if the computer product runs on a computer. Computer program product can be understood according to the present disclosure for example as; a computer program stored on a medium, an embedded system being a comprehensive system with a computer program (e.g. electronic device with a computer program), a network of computer implemented computer programs (e.g. client/server-system, cloud computing system etc.), or a computer on which a computer program is loaded, runs, is stored, is executed or developed.

The term "machine-readable medium" as is used herein, refers in certain embodiments of the present disclosure to a medium, which contains data or information interpretable by software and/or by hardware. The medium may be a data medium, such as a floppy disk, a CD, DVD, a USB stick, a flashcard, an SD card or the like.

A computer program according to the present disclosure comprises a program code to initiate the machine-induced steps of the method according to the present disclosure, if the computer program runs on a computer. According to the present disclosure, a computer program can, for example, be taken to mean a physical, distributable software-product, which comprises a program.

It applies to the digital storage medium according to the present disclosure, the computer program product according to the present disclosure and the computer program according to the present disclosure, that all, some or several of the automatically carried out steps of the method according to the present disclosure are initiated. This applies in interaction, particularly with a detection device according to the present disclosure and/or a provided blood treatment apparatus as herein described, in particular, a blood treatment apparatus, which is used in the method according to the present disclosure.

In all of the following, the use of the expression "may be" or "may have" and so on, is to be understood synonymously with "preferably is" or "preferably has," and so on respectively, and is intended to illustrate an embodiment according to the present disclosure.

Whenever numerical words are mentioned herein, the person skilled in the art shall recognize or understand them as indication of a numerical lower limit. Unless it leads the person skilled in the art to an evident contradiction, the person skilled in the art shall comprehend the specification for example of "one" as encompassing "at least one". This understanding is also equally encompassed by the present disclosure as the interpretation that a numeric word, for example, "one" may alternatively mean "exactly one", wherever this is evidently technically possible for the person skilled in the art. Both are encompassed by the present disclosure and apply herein to all used numerical words.

When an embodiment is mentioned herein, it is then an exemplary embodiment according to the present disclosure.

When "programmed" or "configured" is mentioned herein, it is also disclosed that these terms are interchangeable.

Whenever a method step is mentioned, the present disclosure also encompasses the corresponding programming or configuring of a suitable apparatus or a section thereof.

The term "hydrophobic filter" is used synonymously in several embodiments for a section of the pressure measuring line, which is or comprises a membrane and vice versa. These terms can therefore be herein interchangeable. The membrane may be hydrophobic, and particularly, air-permeable and liquid-impermeable.

Advantageous further developments of the present disclosure are each subject-matter of the dependent claims and embodiments.

Embodiments according to the present disclosure may comprise one or more of the following features.

The herein mentioned bubble trap may be an arterial and/or a venous bubble trap.

In any embodiments the previously stated deviation variable applies as an alternative for any dispersion parameter, such as for the variance, for the standard deviation or the empirical standard variation. In such embodiments according to the present disclosure the deviation variable is a variance, a dispersion parameter, a standard deviation or the like. These terms and subject-matter are also encompassed within the present disclosure.

In some embodiments the deviation variable is defined as the average squared deviation of the current pressure value of an averaged pressure value. The average pressure value may be the average value of the last pressure values measured via the pressure measurement line, e.g. the last five values, or all values, which were measured within the last predetermined period of time from, for example, 0.5 seconds, 1 second, 1.5 seconds and so on.

In some embodiments the deviation variable may be calculated in analogy with calculating the variance in stochastics.

$$\delta^2 = \frac{1}{n} \sum_{i=1,n} ((x_i - x_m)^2),$$

with
n=predetermined number of measurement values, e.g. 5
i=running index across all measurement values
$x_i$=i-th measurement value
$x_m$=average value of all n measurement values
$\delta^2$=deviation variable or deviation degree For example, every 100 ms a pressure measurement value of the venous pressure may be recorded and stored on a dialysis machine. The observation time interval for analyzing the pressure signal is, in this example, 0.5 s, by which time a characteristic section of the pressure course can already be detected. In the example, this results in the predetermined number n as 5 (n=5) measurement values for the observation time interval or in the observation interval. Therefore, 5 measurement values are recorded and the average value $x_m$ of all 5 measurement values is calculated. Then, using the 5 (single) measurement values and the average value $x_m$, the deviation degree is calculated.

Optionally, the calculation approach is formulated so that the deviation is shown exaggerated. This is the case in an embodiment using the quadratic approach, as well as after a mathematical operation in which the deviation is taken into account with an exponent greater than 2 (two) or with a sufficiently large multiplier.

In some embodiments, when measuring a pressure in the pressure measuring line or a pressure change over time, using the pressure sensor, the peak value of the pressure signal is always measured. If the pressure fluctuates, e.g. periodically, possibly due to pressure influences resulting from the movement of the rotor of a blood pump, embodied as a roller pump, the pressure can repeatedly rise and fall again and therefore move between an upper maximum value and a lower minimum value.

The precision of the pressure measurement can thereby be increased in that according to the present disclosure only maximum values or minimum values are considered, for example, when determining an average value from the past pressure measurements, and/or when measuring the actual pressure value.

Instead of maximum values or minimum values, average pressure values can be used, which each lie between the maximum and the minimum value. From these average pressure values of the individual pressure signal, the average value mentioned herein can also be calculated as the expected value.

Furthermore, according to the present disclosure, the rotor position of individual pumps, e.g. the blood pump, can be taken into account when measuring the actual pressure value. Therefore, provision may be made to always measure the pressure when the blood pump (again) assumes a certain rotor position. The latter can be ensured by the use of a corresponding sensor, e.g. a magnetic field sensor or a Hall sensor and the evaluation of its measurements.

In several embodiments, the pressure measuring line according to the present disclosure comprises several lumen sections each having a first lumen geometry and/or several lumen sections each having a second lumen geometry.

In some embodiments, the pressure measuring line according to the present disclosure comprises lumen sections that are separate from each other each having the first lumen geometry.

In several embodiments, the pressure measuring line according to the present disclosure comprises lumen sections that are separate from each other each having the second lumen geometry.

In some embodiments, lumen sections having a first lumen geometry may alternate with lumen sections having a second lumen geometry. Due to the different lumen geometries, which are provided in the pressure measuring line, the liquid level in the different lumen sections increases at different speeds. The continuous dependency between filling level and volume is thus eliminated and can serve to define threshold values for a deviation variable, yet to be determined, by which in turn the filling level of the pressure measuring line can be determined.

In several embodiments the pressure measuring line comprises a further connector that is embodied to connect the pressure measuring line to a, particularly venous, chamber. This chamber may be a blood chamber.

In certain embodiments the lumen sections having a first and/or second lumen geometry are not part of the pressure measuring line connector and/or are not directly connected to such a connector.

In some embodiments the pressure measuring line of the extracorporeal blood tubing set is connected to the, particularly venous, blood chamber.

In certain embodiments of the detection device, the evaluation by said method, is or comprises evaluating, a conclusion reached about the pressure measurement line.

In several embodiments the method encompasses providing a completed collection of minimum values, maximum values, patterns, characteristics, and/or courses of deviation variables or variations in the deviation variables over time that have been collected from one or more predetermined, mutually different pressure measuring lines or characterise these. Furthermore, the evaluation is or comprises a verification of whether the deviation variable or its course is included in the completed collection.

In some embodiments of the detection device the result of the conclusion reached through the evaluation of the method indicates or is that there is a risk of the membrane and/or the sensor getting wet, and/or that a liquid level in the pressure measuring line unduly rises, and/or reaches a predetermined height or alternatively has exceeded it.

In several embodiments of the detection device, when a conclusion is reached that there is a risk of the membrane and/or the sensor getting wet, or that a liquid level in the pressure measuring line is rising or has risen unduly an error message or an alarm is triggered. In this way, the conclusion reached may also result in an interruption or discontinuation of an ongoing treatment procedure, or initiate an interruption or discontinuation, for example, by or after a prompt to the user.

In some embodiments the method of the detection device according to the present disclosure comprises as a further step an interruption or termination of an (ongoing) blood treatment using the blood treatment apparatus. The interruption or termination occurs in these embodiments, when the conclusion reached about the connection is that there is a risk of the membrane or the sensor getting wet, a predetermined height of the level has been exceeded, or that the deviation variable or its course is not included in the completed collection.

In several embodiments the method of the detection device according to the present disclosure comprises, as further steps, that when a conclusion is reached that there is a risk of the membrane and/or the sensor getting wet, or that the liquid level in the pressure measuring line is rising or has risen unduly measures are taken via the blood treatment device in order to lower the liquid level in the pressure measuring line and/or in the, in particular venous, blood chamber or in the, particular venous, bubble trap, which is in, particularly direct, fluid communication with the pressure measuring line.

In several embodiments the measures taken via the blood treatment apparatus to reduce the liquid level in the bubble trap comprise a displacement of a part of the liquid with gas, e.g. using air from the compressed air device or compressed air source, or consist thereof.

This measure can be automatically initiated by the detection device or the blood treatment apparatus. In this way, the level in the pressure measuring line is lowered before there is a risk of the membrane getting wet.

Other measures may alternatively or additionally also be taken such as an error message, an alarm, an interruption of the treatment or the like and may optionally run automatically, e.g. via the detection device or the blood treatment apparatus.

In some embodiments the method comprises the disabling of all treatment modalities of the provided blood treatment apparatus and/or restricting the treatment parameters of feasible blood treatment procedures via the provided blood treatment apparatus. The disabling occurs in these embodiments, if the conclusion reached about the connection is that the membrane or the sensor has gotten wet, a predetermined height of the level has been exceeded and/or that the deviation variable and/or its course are not included in the completed collection.

In several embodiments, the blood treatment apparatus of the detection device is embodied as an apparatus for apheresis or dialysis, again in particular for hemodialysis, hemofiltration, hemodiafiltration.

In some embodiments, the detection device comprises at least one display device or is in signal communication to it in order to display a result of the execution of the method. The detection device is programmed to output corresponding signals to display the result on the display device. The display device may be a display, an error display or the like.

In several embodiments, the blood treatment apparatus is embodied as an apparatus for apheresis or dialysis, again in particular for hemodialysis, hemofiltration, hemodiafiltration.

In some exemplary embodiments according to the present disclosure, the detection device comprises at least one alarm device, which is configured or programmed to output an alarm when the result from executing the method is that the hydrophobic membrane is likely to get wet. Alternatively, it is in signal transmission with such an alarm device.

In some exemplary embodiments according to the present disclosure, the detection device is a control device and/or a performance test monitor or comprises the like in each case.

In certain embodiments, the evaluation of the method is or encompasses reaching a conclusion about the pressure measuring line.

In several embodiments of the method the conclusion reached is or indicates that there is a risk of the membrane and/or the sensor getting wet, and/or that a liquid level in the pressure measuring line is rising, and/or a predetermined level has been reached.

In several embodiments of the method, when a conclusion is reached that there is a risk of the membrane and/or the sensor getting wet, or that a liquid level in the pressure measuring line is rising or has risen unduly, an error message or an alarm is triggered. In this way, the conclusion reached may also result in an interruption or discontinuation of an ongoing treatment procedure, or initiate an interruption or discontinuation, for example, by a prompt or coupled with a prompt to the user.

In some embodiments of the method, an interruption of an (ongoing) blood treatment using the blood treatment apparatus is encompassed as a further step. This may apply in particular to such a blood treatment in which the extracorporeal blood tubing set is used or should be used for the purposes intended. The interruption or termination occurs, in particular, in these embodiments when the conclusion reached about the connection is that there is a risk of it getting wet, or the membrane or the sensor getting wet, that a liquid level in the pressure measuring line is rising or has risen unduly, or that the deviation variable or its course is not included in the completed collection.

The taking of measures to lower the liquid level in the bubble trap via the blood treatment apparatus may also be encompassed as a further step in certain embodiments of the method.

In several embodiments of the method, the blood treatment apparatus is embodied as an apparatus for apheresis or dialysis, again in particular for hemodialysis, hemofiltration, hemodiafiltration.

In several embodiments, the air pressure in the pressure measuring line and consequently also in the, particularly venous, blood chamber is increased via a compressor, and the, particularly venous, clamp is opened so that the liquid level drops and therefore, the membrane and/or the pressure sensor are prevented from getting wet. Alternatively or additionally, an ongoing blood treatment may be interrupted and the user may be requested to confirm the continuation of the treatment.

In several embodiments, the method does not include blowing out the membrane of a hydrophobic filter in order to restore the functionality of the filter using a compressed air source connected to it.

In some embodiments, the method according to the present disclosure terminates prior to determining that the membrane of the hydrophobic filter is clogged.

In several embodiments, values of the deviation variable which are equal to zero or absence of fluctuations in the deviation variable are not used to reach a conclusion as to a risk of the membrane and/or the sensor getting wet.

In some embodiments, amplitude fluctuations of the pressure, and in particular periodically recurring amplitude fluctuations, are not recorded and/or used as criterion for monitoring the pressure measurement line or the pressure measurement arrangement.

In several embodiments, the method does not encompass inferring on the correct function of the pressure measurement line or the pressure measurement arrangement due to the presence of amplitude pressure fluctuations.

In several embodiments, the pressure measuring line comprises no pump, in particular no vacuum pump, and/or no waste container nor is it connected in fluid communication therewith. Most particularly, the pressure measuring line comprises no such pump between its connector for connecting it to the blood treatment apparatus and an end which is provided for connecting it to a blood tubing set, e.g. to a blood chamber thereof.

In some embodiments, the membrane is not suitable, provided and/or used for filtering out constituents, particularly not solid and/or liquid constituents such as wound secretion, from a fluid stream.

Any or all embodiments according to the present disclosure may comprise one or several of the aforementioned or following advantages.

In this way, a higher level of safety is achieved for the patient because according to the present disclosure, safety-relevant functions of the blood tubing set used are ensured, namely the possibility of the correct pressure measurement and with it of the blood treatment apparatus.

According to the present disclosure, a technical error on the sensor (the pressure sensor and/or the hydrophobic membrane getting wet) is detected before it happens, avoiding the unnecessary excessive use of disposable items that would arise when replacing the wet pressure sensor and possibly the corresponding pressure measuring line or even the entire extracorporeal blood tubing set.

It also helps to save time that would otherwise be needed to replace a wet pressure sensor and/or the entire blood tubing set.

The pressure measuring line filling with blood and consequently the membrane and/or sensors getting wet, which results in a necessary replacement of the pressure measuring line, is advantageously avoided. Thereby, the risk of contaminating the dialysis machine is also reduced.

By the method according to the present disclosure, an increase of blood in the pressure measuring line may also be detected.

BRIEF DESCRIPTION OF THE FIGURES

The present disclosure is, in the following, exemplarily explained with regard to the accompanying drawings in which identical reference numerals refer to the same or similar components. The following applies in the partly highly simplified figures.

DETAILED DESCRIPTION

Figure 1:
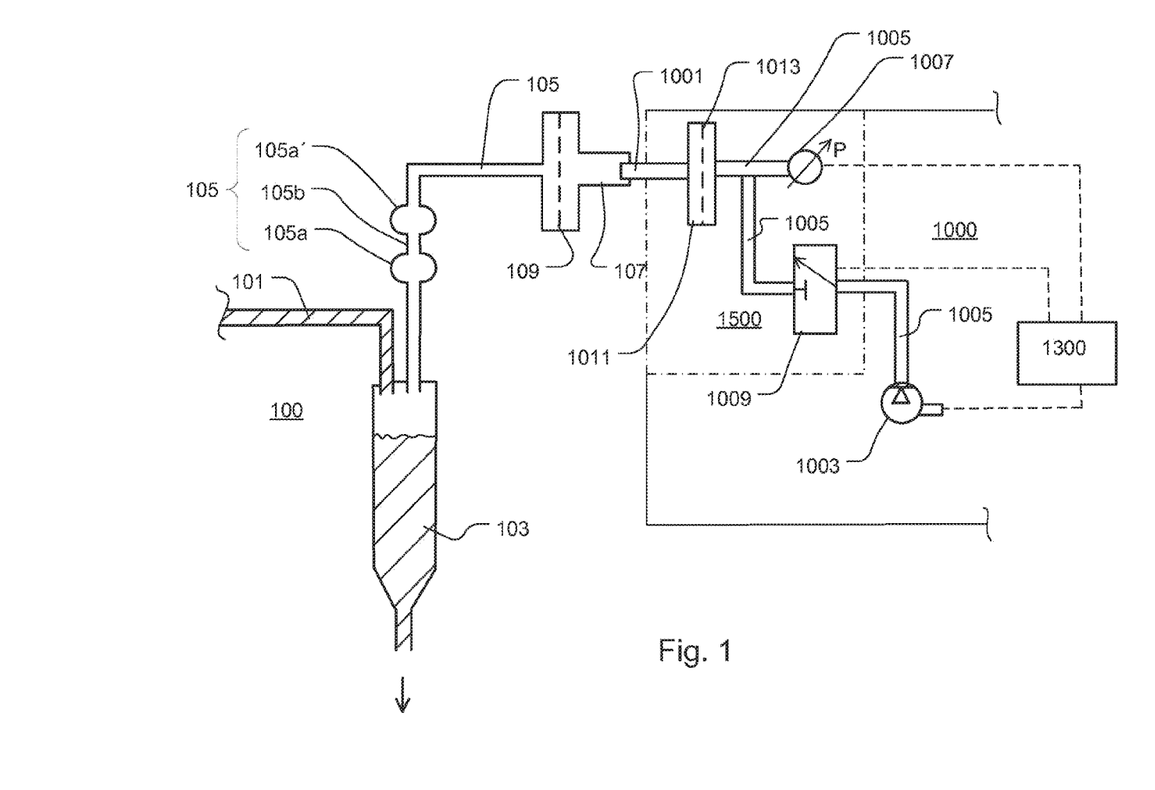
FIG. 1 shows a simplified schematic graph of a blood treatment apparatus according to the present disclosure and a first pressure measuring line of a blood tubing set according to the present disclosure in a first embodiment.

FIG. 1 shows in a very simplified schematic, sections of a blood treatment apparatus 1000 according to the present disclosure as well as sections of a blood tubing set 100 according to the present disclosure.

The inventive concepts of the present disclosure are explained herein, and in particular in the following, with reference to apparatuses according to the present disclosure, which are located on the venous side of the blood tubing set. The disclosure is not limited to its use only on the venous side of a blood tubing set.

The extracorporeal blood tubing set 100, which optionally, may extend in sections outside and inside of a blood cassette—not shown—, comprises a venous patient line 101 and, optionally, a venous blood chamber 103. During use a through-flow of blood in the patient line 101 occurs typically towards the patient, in the direction of the arrows as indicated.

A pressure measuring line 105 according to the present disclosure is connected to the blood tubing set 100 (or a part thereof). In FIG. 1 this pressure measuring line 105, purely illustratively, exits from the venous blood chamber 103, here embodied as a bubble trap. The pressure measuring line 105 may be the return pressure measuring line. It may be an "open line".

The pressure measuring line 105 optionally comprises a connector 107, which is provided and embodied accordingly, to connect the pressure measuring line 105 to, for example, a compressed air outlet 1001 of the blood treatment apparatus 1000. The connector 107 and the compressed air outlet 1001 are, purely optionally, female or male halves of a Luer-lock-connector with a female or male sealing cone or halves of a corresponding Luer-lock-connector with or without additional safety thread.

The compressed air outlet 1001 may be in or on, an outside wall of the blood treatment apparatus 1000, for example, in its housing wall.

The connector 107 of the pressure measuring line 105, or another section of the pressure measuring line 105, which when the pressure measuring line 105 is in use, lies in an area of the pressure measuring line 105 through which air flows or through which air can flow, comprises an air-permeable membrane 109. The air-permeable membrane 109 is embodied, purely as an example, as a hydrophobic membrane or as a hydrophobic filter. The air-permeable membrane 109 is also known to the person skilled in the art by the name "transducer protector" or when abbreviated as "TP".

The blood treatment apparatus 1000 comprises a compressor 1003 as an example of a compressed air device or a compressed air source.

Compressor 1003 and compressed air outlet 1001 are, for example, connected in fluid communication via a compressed air line 1005. Optionally, the compressor 1003 may comprise additional valves for a use other than that described herein.

A pressure sensor 1007 and, purely illustratively, an optional switch valve 1009 (alternatively or additionally a choke, a switch, a lock and/or similar) are provided in or on the compressed air line 1005.

As can be seen in FIG. 1, the pressure sensor 1007 is preferably integrated into the compressed air line 1005 or is in suitable fluid communication to it, so that it can measure the pressure P in the compressed air line 1005 caused by the operation of the compressor 1003, if the switch valve 1009 (if provided) is switched accordingly and if the compressor 1003 is active, i.e. switched on. The pressure sensor 1007 may be the return pressure sensor.

Purely as an example, the compressed air line 1005 runs through an optionally provided protective filter 1011, which in turn comprises a, preferably hydrophobic, air-permeable membrane 1013 positioned in the running flow.

The blood treatment apparatus 1000 comprises a detection device 1300. As indicated by dashes, this is, exemplarily, connected in signal communication to the compressor 1003, the pressure sensor 1007 and/or the switch valve 1009.

As indicated by dashed-dotted lines, at least the compressed air outlet 1001 and pressure sensor 1007 may be part of the independent pressure measuring unit 1500, which is connected to the blood treatment apparatus 1000, optionally, the switch valve 1009 and the protective filter 1011, when provided, may also be part of the above mentioned apparatus.

As can be seen in FIG. 1, the pressure measuring line 105 comprises at least one first lumen section 105a and directly adjacent to this a second lumen section 105b.

The first lumen section 105a comprises a first lumen geometry, the second lumen section 105b comprises a second lumen geometry. The first and the second lumen geometries differ from each other in at least their diameters, in that the first lumen section 105a diameter is bigger than that of the second lumen section 105b. The first lumen section 105a can therefore be referred to as an extension or compartment, the second lumen section 105b as a bottleneck.

In addition to the first lumen section 105a the pressure measuring line 105 comprises a further lumen section 105a'. This also has a bigger diameter than the directly adjacent second lumen section. The further lumen section 105a' may have the same geometry and/or the same diameter as the first lumen section 105a. The lumen sections 105a and 105a' will be now on referred to as "first lumen sections".

The extracorporeal blood tubing set 100, along with the aforementioned components, optionally further comprises an arterial line section which is in fluid connection to a patient, not illustrated, and to a blood treatment apparatus, here exemplarily a blood filter or a dialyzer, also not illustrated. The blood filter comprises a dialysis liquid chamber and a blood chamber, which are separated from each other by a mostly semi-permeable membrane.

The blood treatment apparatus 1000, shown only through some of its devices and schematically represented in FIG. 1, further comprises a blood pump. During the patient's treatment it conveys blood through sections of the extracorporeal blood circuit 100 and towards the blood filter or dialyzer.

Using a pump for dialysis liquid, which may be embodied as a roller pump or as an otherwise occluding pump, fresh dialysis liquid is pumped from a source along a dialysis liquid inlet line into the dialysis liquid chamber. The dialysis liquid leaves the dialysis liquid chamber as filtrate towards a basin.

A further source with substitute may optionally be provided.

Figure 2:
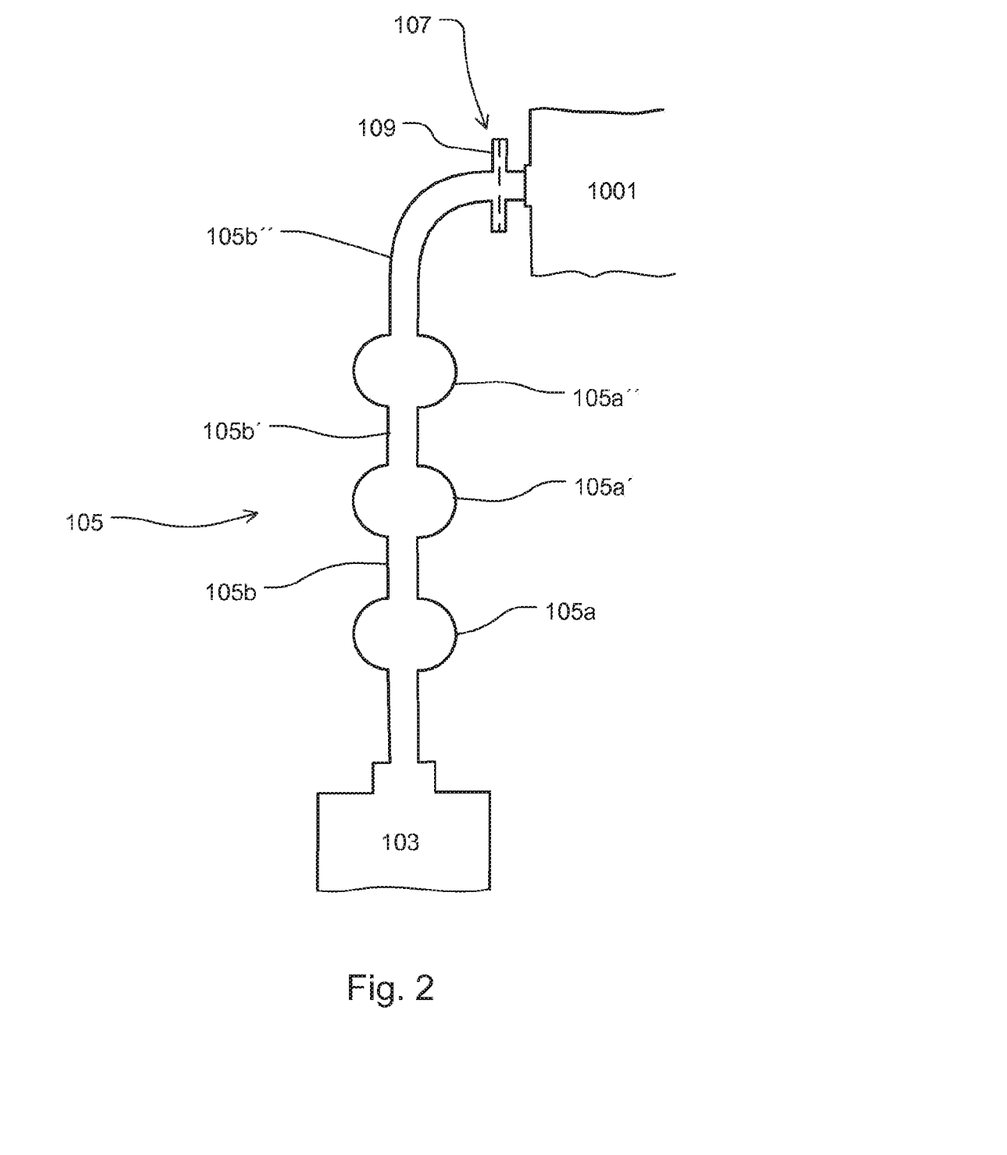
FIG. 2 shows in a simplified schematic a pressure measuring line according to the present disclosure in a second embodiment.

FIG. 2 shows a further embodiment of the pressure measuring line 105 according to the present disclosure. This is connected to a compressed air outlet 1001 and a bubble trap, as an example of a blood chamber 103, see FIG. 1.

The pressure measuring line 105 comprises more, e.g. three lumen sections of a first type, the first lumen sections 105a, 105a' and 105a". They are separated from each other by lumen sections of a second type, second lumen sections 105b, 105b' and 105b". Here, by way of example, lumen sections of the first type alternate with those of the second type.

Figure 3A:
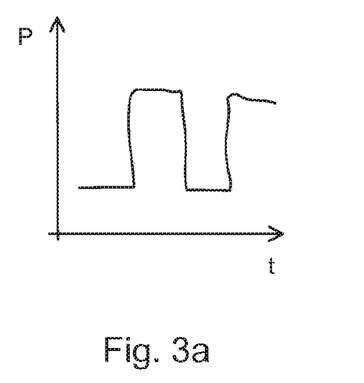
FIG. 3a, 3b each show a diagram, in which is shown pressure measured by the pressure sensor in FIG. 1 according to the present disclosure, over time.
Figure 3B:
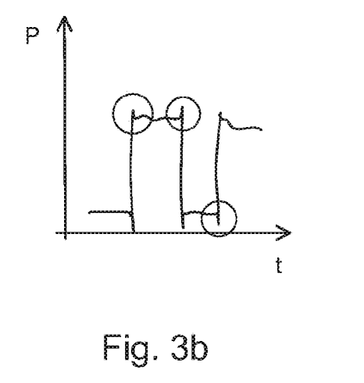

FIGS. 3a and 3b each show a diagram in which the course of the pressure P, measured by the pressure sensor 1007 in FIG. 1 (e.g. in the unit mmHg), is plotted over the time t (e.g. in the unit s as seconds).

FIG. 3a shows the pressure signal, measured using the pressure sensor 1007, when the upper half of the blood chamber 103 is filled with air.

FIG. 3b shows the pressure signal, measured using the pressure sensor 1007, when the blood chamber 103 is filled to the top with liquid, in other words, no air or hardly any air is present.

It can be seen that the overshoots, indicated by circles, during pressure changes in the (semi-)air filled system in FIG. 3a are significantly lower than in FIG. 3b.

This performance is evaluated, according to the present disclosure via the deviation variable, which is here, purely as an example, a squared variable which, possibly, corresponds to the variance or simulates the variance and is therefore exemplarily indicated using $\delta^2$.

The deviation variable $\delta^2$ is here, exemplarily, the average squared deviation of the current pressure value of an averaged pressure value (e.g. 5 pressure values within 500 ms).

The deviation variable need not be a squared deviation. Therefore, the example in the present figures is certainly not to be taken as limiting.

Figure 4:
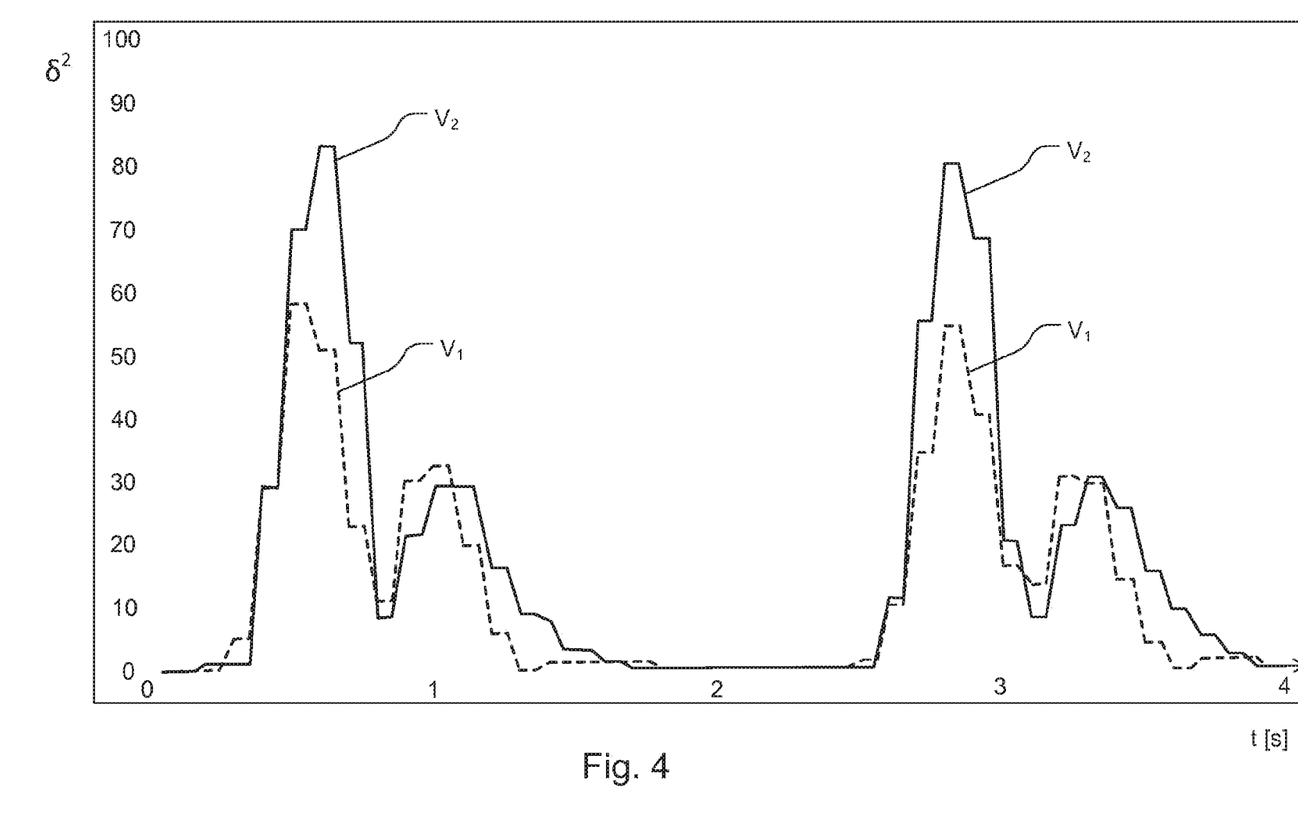
FIG. 4 shows two courses of the deviation variable of the venous pressure in the bubble trap, measured by the pressure sensor in FIG. 1. One with a predominantly air-filled bubble trap and one with a predominantly liquid filled bubble trap, each over time t in seconds [s] at a set blood flow of 100 ml/min.

FIG. 4 shows two courses of the deviation variable $\delta^2$ in FIG. 3 of the venous pressure in the blood chamber 103 measured using the pressure sensor 1007 in FIG. 1. One with a blood chamber 103 predominantly filled with air and one with a blood chamber 103 predominantly filled with liquid, each over time t in seconds [s] with a pre-set blood flow of 100 ml/min.

Thereby, the course V1 (dashes) of the deviation variable $\delta^2$ shows said deviation variable $\delta^2$ having values between 0 and approximately 55. This can be determined by measuring the pressure when there is, comparatively, a lot of air present in the blood chamber 103 which makes an undesirable wetting of the pressure sensor 1007 unlikely.

The course V2 (solid lines) shows a deviation variable $\delta^2$ having values between 0 and approximately 85, conversely to the deviation variable $\delta^2$ which can be determined by measuring the pressure when there is comparatively less air present in the blood chamber 103. This makes an undesirable wetting of the membrane 109 that in turn should protect the pressure sensor 1007 itself from getting wet, more likely. A reason for the different courses V1 and V2 lies in the compressible and therefore dampening properties of the air volume, whereby with an increasing liquid level and thereby decreasing air volume the dampening effect in the pressure measuring line decreases and the deviation variable of the pressure increases. If a lumen section is filled with liquid then this lumen section does not have a dampening effect, due to air and does not contribute to the overall dampening.

Figure 5:
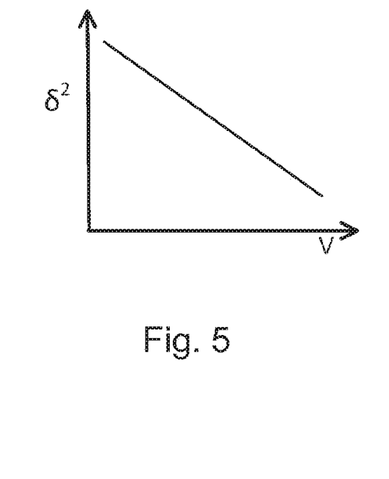
FIG. 5 shows in a simplified diagram that the deviation variable is dependent on the air volume in the pressure measuring line and in the bubble trap.

FIG. 5 in a simple diagram, shows that the air volume V in the pressure measuring line 105 and in the blood chamber 103 is dependent on the deviation variable $\delta^2$.

Figure 6:
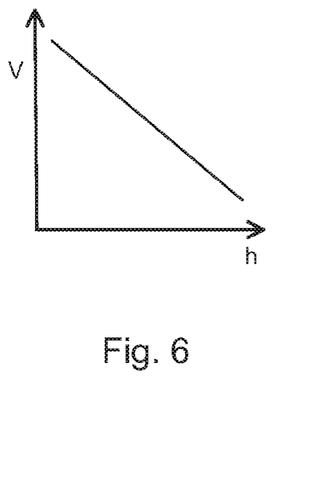
FIG. 6 shows in a simplified diagram that the air volume is dependent on the liquid level in the pressure measuring line and in the bubble trap.

FIG. 6 in a simplified diagram, shows that the air volume V is dependent on the liquid level h in the pressure measuring line 105, assuming a constant cross section of the pressure measuring line 105.

The amount of the deviation variable $\delta^2$ therefore depends on the amount of air or the air volume V in the blood chamber 103 and in the pressure measuring line 105, as is shown in FIG. 5. The air volume V, which is present in the pressure measuring line 105, is again linear to the height h of the liquid level inside the blood chamber 103 as shown in FIG. 6.

Figure 7:
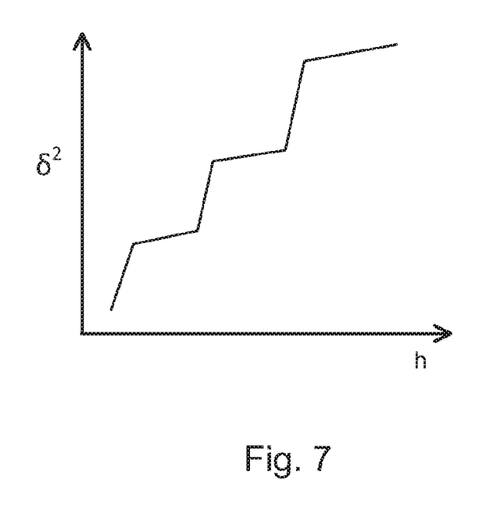
FIG. 7 shows an non continuous increase in the deviation variable in depending on the liquid level owing to the geometry of the pressure measuring line.

To be able to more precisely determine up to what height h the liquid in the pressure measuring line 105 has risen to it is preferable to obtain a non-continuous increase in the deviation variable $\delta^2$ above the filling level, i.e. the height h of the liquid level, as is shown in FIG. 7. It shows the deviation variable $\delta^2$ dependent on the liquid level in the pressure measuring line 105, assuming different cross sections and therefore different volumes along the pressure measuring line 105.

For this purpose, according to the present disclosure, a hose geometry of the pressure measuring line 105 is exemplarily recommended, e.g. as is shown in FIG. 2. It is in the longitudinal section that the geometry is different from the consistently cylindrical shape of known pressure measuring lines.

If a lumen section is filled with liquid, then this lumen section does not comprise a dampening effect due to air and does not contribute to the overall dampening. Due to the different cross sections and therefore volumes per length of the pressure measuring line 105, the liquid level in the sections of the first type (first lumen geometry) rises slower than in those of the second type (second lumen geometry). This eliminates the continual dependency between volume or filling on the one hand and filling level on the other. Therefore, beneficial thresholds can be set for the deviation variable $\delta^2$ on which can be read, to which point or to which section (first type or second type) the liquid has already risen to. Appropriate measures can be initiated based upon these, e.g. as those described herein.

The length of the pressure measuring line 105 (from the connector 107) to the blood chamber 103 is exemplarily between 16.5 and 27.5 cm; preferably 22 cm; the outer diameter is, for example, 5.5 mm; the inner diameter 3.5 mm; the hose material is preferably PVC (polyvinyl chloride). Preferably, a durable bonding of the pressure measuring line 105 is chosen in a socket on the connector 107.

Preferably, the connector 107 of the free end is the female half of a Luer-lock-connector with a female Luer-cone and surrounding external thread.

Preferably, the diameter of the smallest free flow cross section in the female Luer-cone is 2.5 mm; the Luer-cone material is preferably PBT (polybutylene terephthalate).

Preferably, the air-permeable membrane 109 has a free flow diameter in the connector 107, from 10 to 14 mm, ideally 12 mm, that is preferably perpendicular to the flow-direction. The thickness of the air-permeable membrane 109 is preferably for example, around 0.15 mm.

The average pore diameter of the air-permeable membrane 109 (the material of which may be of, amongst others, PTFE (polytetrafluorethylene)), is preferably between 0.1 μm and 0.6 μm, ideally 0.2 μm (micrometre).

The membrane 109 is optionally supported in the connector 107 by radial support ribs, preferably on both sides, to guarantee the air permeability of all of the free cross section and to support the membrane against high pressure.

The machine side compressed air outlet 1001 may be a male half of the Luer-lock-connector with a male Luer-cone and surrounding union nut. It may, advantageously, be completely hygienic as made from stainless steel it is easy to clean.

LIST OF REFERENCE NUMERALS 100 blood tubing set blood circuit
101 venous patient line
103 bubble trap, bubble chamber, drip chamber or, in particular venous, blood chamber
105 pressure measuring line
105a first lumen section
105a' first lumen section
105a" first lumen section
105b second lumen section
105b' second lumen section
105b" second lumen section
107 connector
109 air-permeable membrane
1000 blood treatment apparatus
1001 compressed air outlet
1003 compressed air device, e.g. compressor
1005 compressed air line
1007 pressure sensor
1009 switch valve
1011 protective filter
1013 air-permeable membrane
1300 detection device
1500 pressure measuring unit
h height
P pressure measured
t time
V air volume

The invention claimed is:

1. A pressure measuring line comprising:
a membrane and a connector for connecting the pressure measuring line to a blood treatment apparatus,
wherein the pressure measuring line additionally comprises at least two consecutive lumen sections: a first lumen section and a second lumen section,
wherein the first lumen section comprises a first lumen geometry and the second lumen section comprises a second lumen geometry, whereby the first lumen geometry and the second lumen geometry differ from each other in at least their diameters, and
wherein the connector of the pressure measuring line, or another section of the pressure measuring line, lies in an area of the pressure measuring line through which air flows through when the pressure measuring line is in use.

2. The pressure measuring line according to claim 1, having several lumen sections each having the first lumen geometry and/or several lumen sections each having the second lumen geometry.

3. The pressure measuring line according to claim 2, whereby the several lumen sections each having the first lumen geometry are separate from each other.

4. The pressure measuring line according to claim 3, whereby the several lumen sections each having the second lumen geometry are separate from each other.

5. The pressure measuring line according to claim 4, wherein the several lumen sections each having the first lumen geometry alternate with the several lumen sections each having the second lumen geometry.

6. The pressure measuring line according to claim 1, also comprising a further connector to connect the pressure measuring line to a blood chamber.

7. The pressure measuring line according to claim 1, wherein the pressure measuring line is part of a blood chamber or is connected to a blood chamber.

8. The pressure measuring line according to claim 1, wherein the pressure measuring line is part of an extracorporeal blood tubing set or is connected to an extracorporeal blood tubing set.

9. The pressure measuring line according to claim 8, wherein the pressure measuring line is connected to the blood chamber.

10. The pressure measuring line according to claim 8, wherein the pressure measuring line is part of a blood treatment apparatus or is connected to at least the extracorporeal blood tubing set.

11. The pressure measuring line according to claim 10, wherein the blood treatment apparatus is embodied as an apparatus for apheresis, hemodialysis, hemofiltration, or hemodiafiltration.

12. A system comprising:
the pressure measuring line according to claim 1,
a detection device programmed to monitor the pressure measuring line, an extracorporeal blood tubing set, wherein the pressure measuring line is a part of the extracorporeal blood tubing set or is connected to the extracorporeal blood tubing set, a blood treatment apparatus, wherein the pressure measuring line is connected to the blood treatment apparatus, wherein the blood treatment apparatus comprises a pressure sensor which is positioned to measure a pressure (P) inside the pressure measuring line;

wherein the detection device is configured to perform following functions:

measuring, using the pressure sensor, the pressure (P) in the pressure measuring line or a change of the pressure over time, and determining a deviation variable ($\delta^2$) of the pressure (P) or of the change of the pressure (P) over time, and evaluating the deviation variable ($\delta^2$) or a change in the deviation variable ($\delta^2$) over time, in each case via a comparison of the determined deviation variable, or the change in the deviation variable ($\delta^2$) with previously measured and/or stored values, threshold values, ranges or courses used therefor.

13. The system according to claim 12, wherein the evaluation is or encompasses reaching a conclusion about the pressure measuring line.

14. The system according to claim 13, wherein the conclusion reached is, or indicates, that there is a risk of the membrane and/or the pressure sensor getting wet, a predetermined height (h) of a liquid level in the pressure measuring line is reached, and/or that the liquid level in the pressure measuring line is rising.

15. The system according to claim 14, wherein, in response to reaching the conclusion that there is the risk of the membrane getting wet, an error message or an alarm is triggered.

16. The system according to claim 13, wherein when the conclusion indicates that there is a risk of the membrane and/or the pressure sensor getting wet and/or a predetermined height (h) of the liquid level has been exceeded, the detection device is further configured to:

interrupt or halt of a blood treatment via the blood treatment apparatus; or take measures, using the blood chamber, to lower a liquid level in the blood chamber.

17. The system according to claim 12, wherein the blood treatment apparatus is an apparatus for apheresis, dialysis, hemodialysis, hemofiltration, or hemodiafiltration.

18. The system according to claim 12, the detection device further comprising or connected to: at least one display device, and wherein the at least one display device is configured to display a result of executing the functions.

19. The system according to claim 12, wherein the blood treatment apparatus comprising or is connected to the detection device.

20. The system according to claim 19, wherein the blood treatment apparatus is embodied as an apparatus for apheresis, hemodialysis, hemofiltration, or hemodiafiltration.

21. A method for monitoring the pressure measuring line of an extracorporeal blood tubing set, the method comprising:

providing a blood treatment apparatus having a connection point which is connected to a pressure measuring line comprising a membrane and a connector connecting the pressure measuring line to the connection point of the blood treatment apparatus, wherein the pressure measuring line additionally comprises at least two consecutive lumen sections: a first lumen section comprises a first lumen geometry and a second lumen section comprises a second lumen geometry, whereby the first lumen geometry and the second lumen geometry differ from each other in at least their diameters, and wherein the connector of the pressure measuring line, or another section of the pressure measuring line, lies in an area of the pressure measuring line through which air flows when the pressure measuring line is in use, wherein the blood treatment apparatus comprising a pressure sensor positioned to measure the pressure (P) in the pressure measuring line;

measuring, using the pressure sensor, the pressure (P) in the pressure measuring line or the change in pressure over time, and determining a deviation variable ($\delta^2$) of the pressure (P) or of a change of the pressure (P) over time, and evaluating the deviation variable ($\delta^2$) or the change in the deviation variable ($\delta^2$) over time, in each case via a comparison of the determined deviation variable ($\delta^2$) or the determined change of the deviation variable ($\delta^2$), with previously measured or stored values, threshold values, ranges or courses.

22. The method according to claim 21, wherein the evaluation is or encompasses reaching a conclusion about the pressure measuring line.

23. The method according to claim 22, wherein the conclusion reached is or indicates that there is a risk of the membrane and/or the pressure sensor getting wet, a predetermined height (h) of a liquid level in the pressure measuring line is reached and/or that the liquid level in the pressure measuring line is rising.

24. The method according to claim 23, wherein in reaching the conclusion that there is the risk of the membrance and/or the pressure sensor getting wet, an error message or an alarm is triggered.

25. The method according to claim 21, further comprising:

interrupting or halting of a blood treatment via the provided blood treatment apparatus;

or:

taking measures, using the blood treatment apparatus, to lower a liquid level in a blood chamber connected to the pressure measuring line;

in each case when reaching a conclusion about the connection is or indicates that there is a risk of the membrane and/or the pressure sensor getting wet and/or that a predetermined height (h) of the liquid level has been exceeded.

26. The method according to claim 21, wherein the blood treatment apparatus is an apparatus for apheresis, hemodialysis, hemofiltration, or hemodiafiltration.

27. A non-transitory computable readable medium for storing instructions, which when executed by a computer, causes the computer to:

measure, using a pressure sensor of a blood treatment apparatus positioned to measure the pressure (P) in the pressure measuring line according to claim 1, the pressure (P) in the pressure measuring line or the change in pressure over time, and determining a deviation variable ($\delta 2$) of the pressure ($\delta 2$) or of the change in pressure (P) over time, and evaluate the deviation variable ($\delta 2$) or a change in the deviation variable ($\delta 2$) over time, in each case via a comparison of the determined deviation variable ($\delta 2$)

or of the change of the deviation variable ($\delta 2$), with previously measured or stored values, threshold values, ranges or courses.

\* \* \* \* \*

UNITED STATES PATENT AND TRADEMARK OFFICE
CERTIFICATE OF CORRECTION

| | |
|---|---|
| PATENT NO. | : 11,571,502 B2 |
| APPLICATION NO. | : 17/049117 |
| DATED | : February 7, 2023 |
| INVENTOR(S) | : Juergen Klewinghaus and Alexander Schroers |

It is certified that error appears in the above-identified patent and that said Letters Patent is hereby corrected as shown below:

In the Claims

Column 16, Line 35, Claim 24, delete "membrance" and insert --membrane--.

Signed and Sealed this
Fourth Day of April, 2023

Katherine Kelly Vidal
*Director of the United States Patent and Trademark Office*